(12) United States Patent
Takemura et al.

(10) Patent No.: US 11,247,023 B2
(45) Date of Patent: Feb. 15, 2022

(54) CATHETER

(71) Applicant: TERUMO KABUSHIKI KAISHA, Tokyo (JP)

(72) Inventors: Tomoaki Takemura, Isehara (JP); Yuya Otake, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 343 days.

(21) Appl. No.: 15/361,179

(22) Filed: Nov. 25, 2016

(65) Prior Publication Data
US 2017/0151417 A1    Jun. 1, 2017

(30) Foreign Application Priority Data

Nov. 26, 2015    (JP) .............................. JP2015-230308

(51) Int. Cl.
*A61M 25/00*    (2006.01)
*A61M 5/00*    (2006.01)
(Continued)

(52) U.S. Cl.
CPC ........... *A61M 25/0097* (2013.01); *A61F 2/95* (2013.01); *A61L 29/041* (2013.01); *A61M 5/007* (2013.01);
(Continued)

(58) Field of Classification Search
CPC .......... A61M 25/0097; A61M 25/0045; A61M 25/005; A61M 25/0052; A61M 25/10;
(Continued)

(56) References Cited

U.S. PATENT DOCUMENTS 4,781,703 A    11/1988 Walker et al.
4,802,947 A *  2/1989 Bartholomew ... A61M 25/0014
                                        156/380.5
(Continued)

FOREIGN PATENT DOCUMENTS

CN    104053471 A    9/2014
CN    104548315 A    4/2015
(Continued)

OTHER PUBLICATIONS

The extended European Search Report dated May 15, 2017, by the European Patent Office in corresponding European Patent Application No. 16199587.3 (8 pgs).

(Continued)

*Primary Examiner* — Lauren P Farrar
*Assistant Examiner* — Hamza A Darb
(74) *Attorney, Agent, or Firm* — Buchanan Ingersoll & Rooney PC

(57) ABSTRACT

A catheter includes: a catheter shaft; and a hub on a proximal side of the catheter shaft. The catheter shaft includes a shaft inner surface inclined portion at a proximal portion, the diameter of which increases proximally such that the shaft inner surface inclined portion forms an angle with the catheter central axis. The hub includes a first hub inner surface inclined portion continuous from the shaft inner surface inclined portion and inclined at the same inclination angle as the shaft inner surface inclined portion, and a second hub inner surface inclined portion proximal of the first hub inner surface inclined portion. The second hub inner surface inclined portion inclination angle differs from the first hub inner surface inclined portion inclination angle. The hub does not cover an inner peripheral surface of the catheter shaft in an interlock portion in which the catheter shaft and the hub are interlocked together.

10 Claims, 9 Drawing Sheets

(51) Int. Cl.
| | |
|---|---|
| *A61M 25/09* | (2006.01) |
| *A61M 25/10* | (2013.01) |
| *A61F 2/95* | (2013.01) |
| *A61F 2/962* | (2013.01) |
| *A61L 29/04* | (2006.01) |
| *B29C 45/00* | (2006.01) |
| *A61M 39/10* | (2006.01) |
| *B29C 45/16* | (2006.01) |
| *B29C 45/26* | (2006.01) |
| *B29C 45/36* | (2006.01) |
| *B29C 45/72* | (2006.01) |
| *A61M 25/01* | (2006.01) |
| *B29K 27/18* | (2006.01) |
| *B29K 105/08* | (2006.01) |
| *B29K 77/00* | (2006.01) |
| *B29K 305/00* | (2006.01) |
| *B29L 9/00* | (2006.01) |
| *B29L 31/00* | (2006.01) |

(52) U.S. Cl.
CPC .... *A61M 25/0014* (2013.01); *A61M 25/0045* (2013.01); *A61M 25/0052* (2013.01); *A61M 25/09* (2013.01); *A61M 25/104* (2013.01); *A61M 39/10* (2013.01); *B29C 45/0005* (2013.01); *B29C 45/16* (2013.01); *B29C 45/2628* (2013.01); *B29C 45/36* (2013.01); *B29C 45/72* (2013.01); *B29C 2045/366* (2013.01); *B29K 2027/18* (2013.01); *B29K 2077/00* (2013.01); *B29K 2105/0827* (2013.01); *B29K 2305/00* (2013.01); *B29K 2995/0073* (2013.01); *B29L 2009/003* (2013.01); *B29L 2031/7534* (2013.01)

(58) Field of Classification Search
CPC ................ A61M 25/104; A61M 39/10; A61M 25/0014; A61M 5/007; A61M 25/09; A61M 2025/0098; A61M 25/0102; A61M 25/0105; A61M 25/0113; A61M 25/0136; A61M 2025/0186; A61M 2205/02; A61F 2/95; A61F 2/962; A61L 29/041; B29C 45/0005; B29C 45/16; B29C 45/2628; B29C 45/36; B29C 45/72; B29C 2045/366; B29K 2027/18; B29K 2077/00; B29K 2105/0827; B29K 2305/00; B29K 2995/0073; B29L 2009/003; B29L 2031/7534

See application file for complete search history.

(56) References Cited

U.S. PATENT DOCUMENTS

| | | | |
|---|---|---|---|
| 2004/0193140 | A1 | 9/2004 | Griffin et al. |
| 2006/0135973 | A1* | 6/2006 | Hawkins ............ A61B 17/3415 606/167 |
| 2009/0157007 | A1 | 6/2009 | McKinnon |
| 2013/0165867 | A1 | 6/2013 | Isaacson et al. |
| 2014/0309533 | A1 | 10/2014 | Yamashita et al. |
| 2014/0358123 | A1* | 12/2014 | Ueda ................ A61M 25/0097 604/510 |
| 2015/0151088 | A1* | 6/2015 | Lim .................. A61M 25/0693 604/247 |
| 2017/0035992 | A1 | 2/2017 | Harding et al. |
| 2017/0135720 | A1* | 5/2017 | Oshida .................. A61M 5/343 |

FOREIGN PATENT DOCUMENTS

| | | |
|---|---|---|
| EP | 0227230 A1 | 7/1987 |
| JP | 2006-513799 A | 4/2006 |
| JP | 2015-019851 A | 2/2015 |
| WO | 2015111680 A1 | 7/2015 |
| WO | 2015161294 A1 | 10/2015 |

OTHER PUBLICATIONS

Office Action (Notice of Reasons for Refusal) dated Jul. 16, 2019, by the Japanese Patent Office in corresponding Japanese Patent Application No. 2015-230308 and an English Translation of the Office Action. (8 pages).

Office Action (First Office Action) dated May 7, 2020, by the State Intellectual Property Office of People's Republic of China in corresponding Chinese Patent Application No. 201610827263.9 and an English Translation of the Office Action. (15 pages).

Office Action (Second Office Action) dated Dec. 28, 2020, by the State Intellectual Property Office of People's Republic of China in corresponding Chinese Patent Application No. 201610827263.9 and an English Translation of the Office Action. (19 pages).

* cited by examiner

CATHETER

CROSS-REFERENCES TO RELATED APPLICATIONS

This application claims priority under 35 U.S.C. § 119(a) to Japanese Application No. 2015-230308 filed on Nov. 26, 2015, the entire content of which is incorporated herein by reference.

TECHNICAL FIELD

The present invention generally relates to a catheter to be inserted into a biological lumen, particularly, to a guiding catheter that guides a medical instrument to a target site in a lumen of a body/living body.

BACKGROUND DISCUSSION

A guiding catheter is used to guide a medical instrument (a balloon catheter, a stent indwelling catheter, or the like), which is inserted into a biological lumen, for example, a blood vessel so as to perform treatment or diagnosis, to a target site. A reduction in the incision at the insertion site of a blood vessel is desired so as to reduce patient burden, and a guiding catheter preferably has a small outer diameter so as to reduce friction between a blood vessel and the guiding catheter. In contrast, a medical instrument inserted into a guiding catheter preferably has a large outer diameter so as to display satisfactory effects in a target site such as a treatment site. For this reason, the guiding catheter into which the medical instrument is inserted is required to have a relatively large inner diameter.

In the related art, a technique of inserting a catheter into an artery of a wrist and treating a coronary artery via transradial intervention (TRI) has been widely performed. In a case where a catheter gains access to an artery of a lower limb through an artery of a wrist via the recently proposed TRI, since the diameter of a blood vessel of the wrist (the inner diameter of a blood vessel in a catheter insertion site) is smaller than that of the lower limb (the inner diameter of a blood vessel in a target site of the catheter), the outer diameter of a medical instrument is relatively large compared to the inner diameter of a guiding catheter. For this reason, in a case where right and left arteries of the lower limb are simultaneously obstructed, if an operator treats one artery via a balloon catheter, and then deflates and pulls a dilated balloon out, and inserts the balloon again, sliding resistance of the catheter against a lumen of a guiding catheter increases, and there is a possibility of causing the occurrence of deformation of or damage to the guiding catheter or the balloon catheter.

Japanese Application Publication No. 2015-19851 discloses a catheter in which a proximal portion of an inner layer of a long tube shaped catheter shaft penetrates into the material of a hub in a connection section between the catheter shaft and the hub, and thus the separation of the inner layer is prevented. In the catheter, even if the separation of the inner layer is prevented, when a medical instrument inserted into a lumen of the catheter is to be pulled out, the material of the hub covering an inner peripheral surface of the inner layer may be separated from the inner layer, or an edge portion of a separated hub material may cause damage to a balloon catheter, which is a problem.

SUMMARY

The catheter disclosed here is configured so that the slide resistance of a medical instrument against a lumen of the catheter can be reduced, and deformation of or damage to the catheter or the medical instrument can be prevented.

The disclosed catheter includes: a catheter shaft in which a lumen is formed; and a hub in which a hub lumen communicating with the lumen is formed, with the lumen defining an inner peripheral surface of the catheter shaft and the hub being provided on a proximal end portion of the catheter shaft. The catheter shaft includes a shaft inner surface inclined portion which is formed on the inner peripheral surface of the proximal portion of the catheter shaft, with the shaft inner surface inclined portion possessing an inner diameter increasing toward a proximal direction such that the shaft inner surface inclined portion forms an inclination angle with respect to a central axis of the catheter. The hub includes a first hub inner surface inclined portion that is continuous from the shaft inner surface inclined portion and that is inclined at an inclination angle with respect to the central axis of the catheter that is the same as the inclination angle of the shaft inner surface inclined portion, and the hub also includes a second hub inner surface inclined portion on a proximal side of the first hub inner surface inclined portion. The second hub inner surface inclined portion possesses an inner diameter which increases toward the proximal direction such that the second hub inner surface inclined portion forms an inclination angle with respect to the central axis of the catheter that is different from the inclination angle of the first hub inner surface inclined portion. The hub does not cover the inner peripheral surface of the catheter shaft in an interlock portion in which the catheter shaft and the hub are interlocked together.

In the catheter having the above-described configuration, since the catheter shaft and the hub are interlocked together at the position of an inclined portion with which a medical instrument is unlikely to come into contact, and the inclination angles of inner peripheral surfaces of the catheter shaft and the hub in the interlock portion with respect to the central axis are the same, the slide resistance of the medical instrument against a lumen of the catheter is reduced. Since the hub does not cover the inner peripheral surface of the catheter shaft in the interlock portion between the hub and the catheter shaft, when a medical instrument or the like is slid against the lumen of the catheter, particularly, when the medical instrument or the like is pulled backward, the separation of hub resin is unlikely to occur, and it is possible to prevent deformation of or damage to the catheter or the medical instrument which is caused by slide resistance or separation.

The catheter shaft may include an inner layer; an outer layer that is disposed an outer peripheral surface side of the inner layer; and reinforcement filaments which are disposed between the inner layer and the outer layer. Since the reinforcement filaments are provided in the catheter shaft, deformation of the catheter shaft is prevented, and separation between the hub and the catheter shaft is unlikely to occur. As a result, it is possible to prevent deformation of or damage to the catheter or a medical instrument. In a case where the hub is molded via injection molding, resin which is the material of the hub is likely to penetrate into the catheter shaft. In contrast, since the reinforcement filaments are provided in the catheter shaft, the proximal portion of the catheter shaft is unlikely to be deformed, and it is possible to prevent the penetration of the resin into a proximal portion of the catheter in the interlock portion. For this reason, separation between the hub and the catheter shaft is unlikely to occur, and it is possible to reduce deformation of or damage to the catheter or a medical instrument.

The reinforcement filaments may be in contact with the hub on a proximal surface of the catheter shaft. As a result, the hub and the catheter shaft are rigidly interlocked together, and the pressure resistance of the catheter and the durability of the catheter against deformation are further improved.

At least a portion of the reinforcement filaments may protrude further toward a proximal side than the inner layer and the outer layer, and may bite into or be embedded in the hub. As a result, the hub and the catheter shaft are more rigidly interlocked together, and the pressure resistance of the catheter and the durability of the catheter against deformation are further improved.

The axial length of a portion of the catheter shaft, in which the shaft inner surface inclined portion is formed, may be set to 0.5 mm or greater and 3.0 mm or less. If the axial length of the portion, in which the shaft inner surface inclined portion is formed, is excessively short, a medical instrument to be inserted may become caught in the interlock portion. If the axial length is excessively long, when the catheter shaft is to be formed, the form of the catheter shaft may be distorted.

The inclination angle of the shaft inner surface inclined portion with respect to the central axis may be set to exceed 0° and to be 13° or less. The central axis of the catheter refers to a longitudinal axis of the lumen which extends from a distal end of the catheter up to a proximal portion of the hub (refer to reference sign X in FIG. 4). If the inclination angle of the shaft inner surface inclined portion with respect to the central axis is set to 0°, when the hub is to be molded via injection molding, the inner pressure of a mold may cause the distortion of the proximal portion of the catheter shaft such that the proximal portion of the catheter shaft collapses inward. If the inclination angle of the shaft inner surface inclined portion with respect to the central axis is excessively large, during injection molding, the resin of the hub may penetrate into the catheter shaft.

The catheter shaft is formed of a material containing polytetrafluoroethylene. As a result, the catheter shaft is unlikely to have affinity with the material of the hub, and is likely to separate therefrom; however, according to the present invention, it is possible to prevent the occurrence of separation.

According to another aspect, a catheter comprises: a catheter shaft possessing a proximal end portion, and an axially extending catheter shaft lumen passing through the catheter shaft, wherein the catheter shaft lumen is surrounded by the inner peripheral surface of the catheter shaft; and a hub fixed to the proximal end portion of the catheter shaft so that a distal end portion of the hub axially overlaps the proximal end portion of the catheter shaft in an overlap region. A hub lumen is inside the hub, the hub lumen possesses an inner peripheral surface surrounding the hub lumen, and the hub lumen communicates with the catheter shaft lumen. A proximal-most end portion of the inner peripheral surface of the catheter shaft includes a first inclined portion possessing an inner diameter gradually increasing at an inclination angle in a proximal direction, and the inner surface of the hub includes a first inclined portion possessing an inner diameter gradually increasing at an inclination angle in the proximal direction, with the inclination angle of the first inclined portion of the inner surface of the hub being the same as the inclination angle of the first inclined portion of the inner peripheral surface of the catheter shaft. A proximal-most end of the first inclined portion of the inner peripheral surface of the catheter shaft and a distal-most end of the first inclined portion of the inner peripheral surface of the hub immediately adjoin one another, and the inner surface of the hub includes a second inclined portion possessing an inner diameter gradually increasing at an inclination angle in the proximal direction. The inclination angle of the first inclined portion of the inner surface of the hub being different from the inclination angle of the second inclined portion of the inner peripheral surface of the hub. The second inclined portion of the inner peripheral surface of the hub is positioned proximally of the first inclined portion of the inner peripheral surface of the hub, and the hub is made of a material that does not cover the inner peripheral surface of the catheter shaft in the overlap portion.

In accordance with another disclosed aspect, a method of making a catheter comprises positioning a catheter shaft in a mold, wherein the catheter shaft possesses a proximal end portion and an axially extending catheter shaft lumen passing through the catheter shaft, with a core pin positioned in the lumen in the catheter shaft lumen. The core pin includes a distal tapered portion inclined relative to a central axis of the catheter shaft at an first inclination angle so that an outer diameter of the catheter shaft gradually increases in a proximal direction, and also includes a proximal tapered portion inclined relative to the central axis of the catheter shaft at a second inclination angle possessing an outer diameter that gradually increases in the proximal direction. The proximal tapered portion is positioned proximal of the distal tapered portion, and the second inclination angle is different from the first inclination angle. The core pin is positioned in the catheter shaft lumen such that a part of the distal tapered portion of the core pin is in the catheter shaft lumen at the proximal end portion of the catheter shaft lumen and an other part of the distal tapered portion of the core pin is outside the catheter shaft lumen on a proximal side of the catheter shaft lumen. The part of the tapered portion of the core pin that is in the catheter shaft lumen at the proximal end portion of the catheter shaft lumen causes the catheter shaft lumen at the proximal end portion of the catheter to be tapered in the same way as the tapered portion of the core pin. The positioning of the catheter shaft in the mold involves positioning the catheter shaft and the core pin so that one part of the mold contacts an axially extending part of the outer surface of the catheter shaft, an other part of the mold contacts an outer surface of the core pin, and an inner surface of the mold between the one part and the other part is spaced from the outer surface of the core pin and the outer surface of the catheter shaft to define a cavity. The method additionally involves filling the cavity with resin so that the resin contacts the outer surface of the other part of the distal tapered portion of the core pin, the outer surface of the proximal tapered portion of the core pin, and the outer surface of the proximal end portion of the catheter shaft. The method further involves allowing the resin in the cavity to cool to produce a resin hub that is fixed to the proximal end portion of the catheter shaft, and removing the catheter shaft and resin hub from the mold and removing the core pin from the catheter shaft lumen.

DETAILED DESCRIPTION

Figure 1:
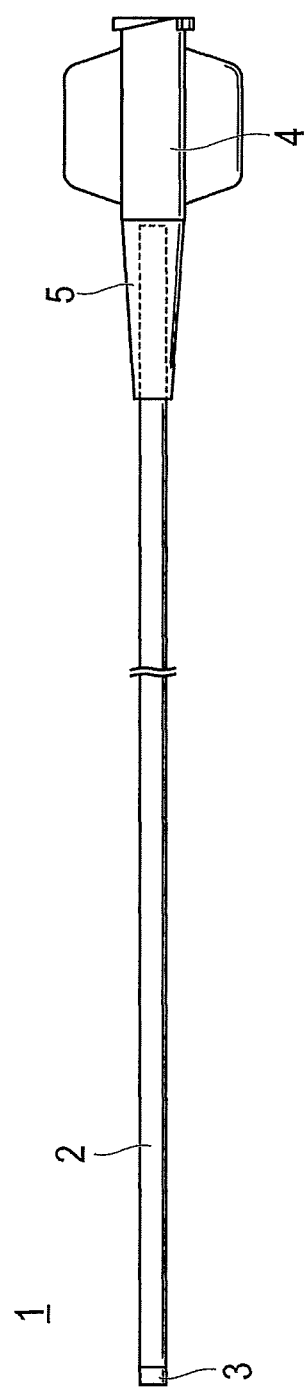
FIG. 1 is a plan view illustrating a catheter of an embodiment.

Set forth below reference to the drawings is a detailed description of an embodiment of a catheter and a method for making the catheter representing an example of the inventive catheter and method disclosed here. For illustrative purposes, dimensional ratios in the drawings may be exaggerated and may be different from actual ratios. In the following description, a hand-side of a catheter is referred to as a "proximal side" or "proximal end", and a side inserted into a living body is referred to as a "distal side" or "distal end".

A catheter 1 of the embodiment is used as a guiding catheter that guides a medical instrument, for example, a balloon catheter, a catheter (stent transport catheter) that transports a stent to a stenosed site with the diameter (outer diameter) of the stent decreased, and widens and maintains the stenosed site by increasing the diameter (outer diameter) and indwelling the stent at the stenosed site, or a guide wire to a target site such as a stenosed site of a blood vessel of a lower limb through a blood vessel of an arm such as a radial artery.

Figure 2:
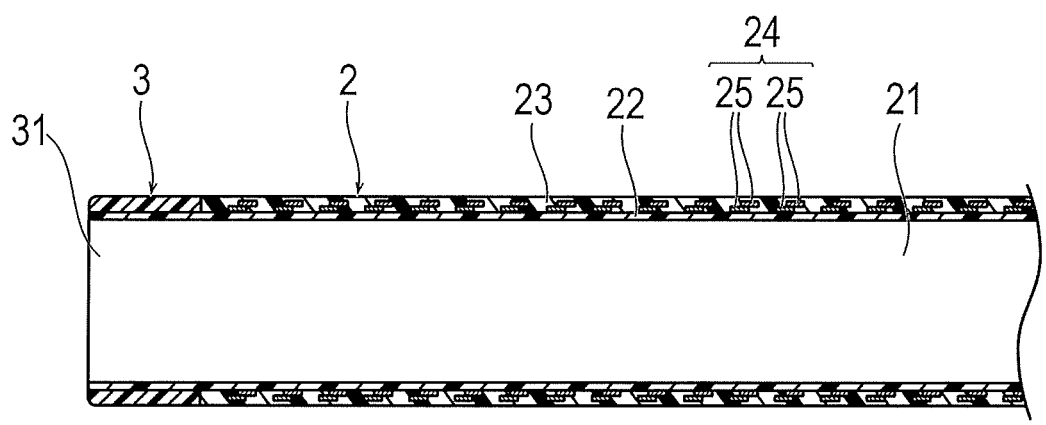
FIG. 2 is a sectional view illustrating the catheter of the embodiment.

As illustrated in FIGS. 1 and 2, the catheter 1 includes a catheter shaft 2; a very flexible soft tip 3 that is provided on a distal side or at a distal end of the catheter shaft 2 so that the distal end of the shaft 2 includes the tip 3; a hub 4 that provided on a proximal side or at the proximal end of the catheter shaft 2; and an anti-kink protector (covered member) 5 with which an interlock portion between the catheter shaft 2 and the hub 4 is coated.

The catheter shaft 2 is configured of a flexible tube shaped body. A lumen (catheter shaft lumen) 21 is formed in a substantially central portion of the catheter shaft 2 over the entire length of the catheter shaft 2. That is, the axially extending lumen passes through the catheter shaft The lumen 21 is open in a distal end opening portion 31 at a distal end of the soft tip 3.

The catheter shaft 2 includes an inner layer 22 possessing an inner surface facing towards and surrounding the lumen 21; an outer layer 23 possessing an outer surface constituting the outer surface of the catheter shaft 2; and a reinforcement portion 24 (reinforcement that is positioned between the inner surface of the inner layer 22 and the outer surface of the outer layer 23. In the illustrated embodiment, the reinforcement portion 24 is positioned on the outer surface of the inner layer 22 and is embedded in the outer layer 23.

Examples of the material of the outer layer 23 include various thermoplastic elastomers such as a styrene elastomer, a polyolefin elastomer, a polyurethane elastomer, a polyester elastomer, a polyamide elastomer, a polybutadiene elastomer, a trans-polyisoprene elastomer, a fluororubber elastomer, and a chlorinated polyethylene elastomer. A combination of one or two or more (polymer alloy, polymer blend, laminated body, or the like) of these may be also used as the material.

At least a portion of the inner layer 22, which comes into contact with a medical instrument such as a treatment device or a guide wire when the medical instrument is inserted into the lumen 21, is preferably made of a low friction material. As a result, the medical instrument inserted into the catheter shaft 2 can be moved inside the catheter lumen with lower slide resistance, and the low friction material contributes to an improvement in operability. Naturally, the entirety of the inner layer 22 may be made of a low friction material. Fluorine resin such as polytetrafluoroethylene (PTFE) is an example of the low friction material.

Figure 3:
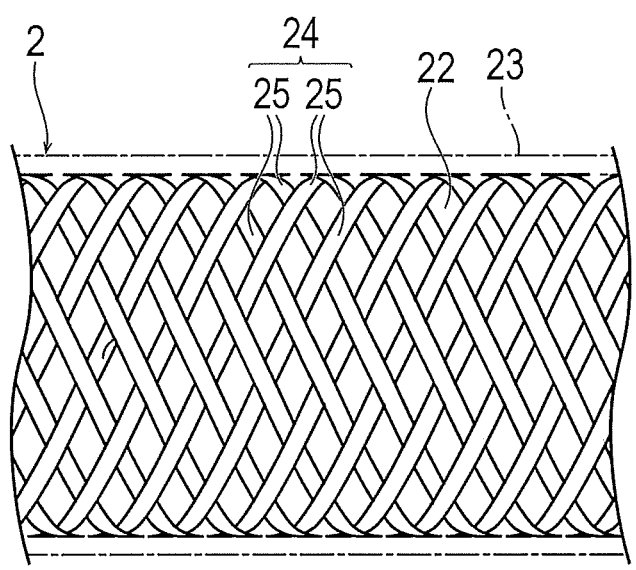
FIG. 3 is a see-through view in which reinforcement filaments are observed through an outer layer of the catheter of the embodiment.

The reinforcement portion 24 reinforces the catheter shaft 2. As illustrated in FIGS. 2 and 3, the reinforcement portion 24 includes multiple reinforcement filaments 25. The resin of the outer layer 23 penetrates into gaps between the multiple reinforcement filaments 25 of the reinforcement portion 24. It is possible, as an alternative, for the reinforcement filaments 25 to be embedded in the inner layer 22 so that the resin of the inner layer 22 penetrates into gaps between the multiple reinforcement filaments 25. In the illustrated embodiment, for example, the reinforcement filaments 25 have a helical shape or a mesh shape. The reinforcement filaments 25 are made of metal such as stainless steel or Nickel-titanium alloy. A specific example of the reinforcement filament 25 is a flat filament that is obtained by flattening a stainless steel filament such that the thickness of the stainless steel filament in a radial direction of the catheter shaft 2 is decreased. The reinforcement filament 25 is not limited to a flat filament, and may be a round filament or an elliptical filament. Each of the reinforcement filaments 25 may be two or more bundles of reinforcement filaments.

Since the catheter shaft 2 includes the reinforcement portion 24, rigidity and strength of the catheter shaft 2 can be sufficiently ensured without the wall thickness of the catheter shaft 2 being increased, that is, while the inner diameter of the catheter shaft 2 is set to be relatively large. As a result, it is possible to obtain the catheter 1 into which a medical instrument having a relative large outer diameter can be inserted, which has good pushability and good torque transmission performance, and in which kink or collapse is unlikely to occur.

At least a portion of the catheter shaft 2 may be curved. Since at least a portion of the catheter shaft 2 is curved, the catheter 1 can be suitably shaped for an insertion site, or can be easily engaged with a target site depending on use of the catheter 1.

The soft tip 3 illustrated in FIGS. 1 and 2 is made of a very flexible material, and the distal end of the soft tip 3 preferably has round shape. Since the catheter 1 is provided with the soft tip 3, the catheter 1 is capable of smoothly and safely traveling even inside a curved, bent, or bifurcated blood vessel. Examples of the material of the soft tip 3 include various rubber materials such as natural rubber, isoprene rubber, butadiene rubber, chloroprene rubber, silicone rubber, fluororubber, styrene-butadiene rubber, or various thermoplastic elastomers such as a styrene elastomer, a polyolefin elastomer, a polyurethane elastomer, a polyester elastomer, a polyamide elastomer, a polybutadiene elastomer, a trans-polyisoprene elastomer, a fluororubber elastomer, and a chlorinated polyethylene elastomer.

The catheter shaft 2 preferably has an outer diameter of 1 mm or greater and 3 mm or less. If the outer diameter is excessively large, when the catheter shaft 2 is inserted into and moved inside a blood vessel such as a radial artery, operability may deteriorate, and burdens on a patient may increase.

The catheter shaft 2 preferably has an inner diameter of 1 mm or greater and 3 mm or less. If the inner diameter is excessively small, it may be difficult to insert a medical instrument into the catheter 1, and operability may deteriorate.

Figure 4:
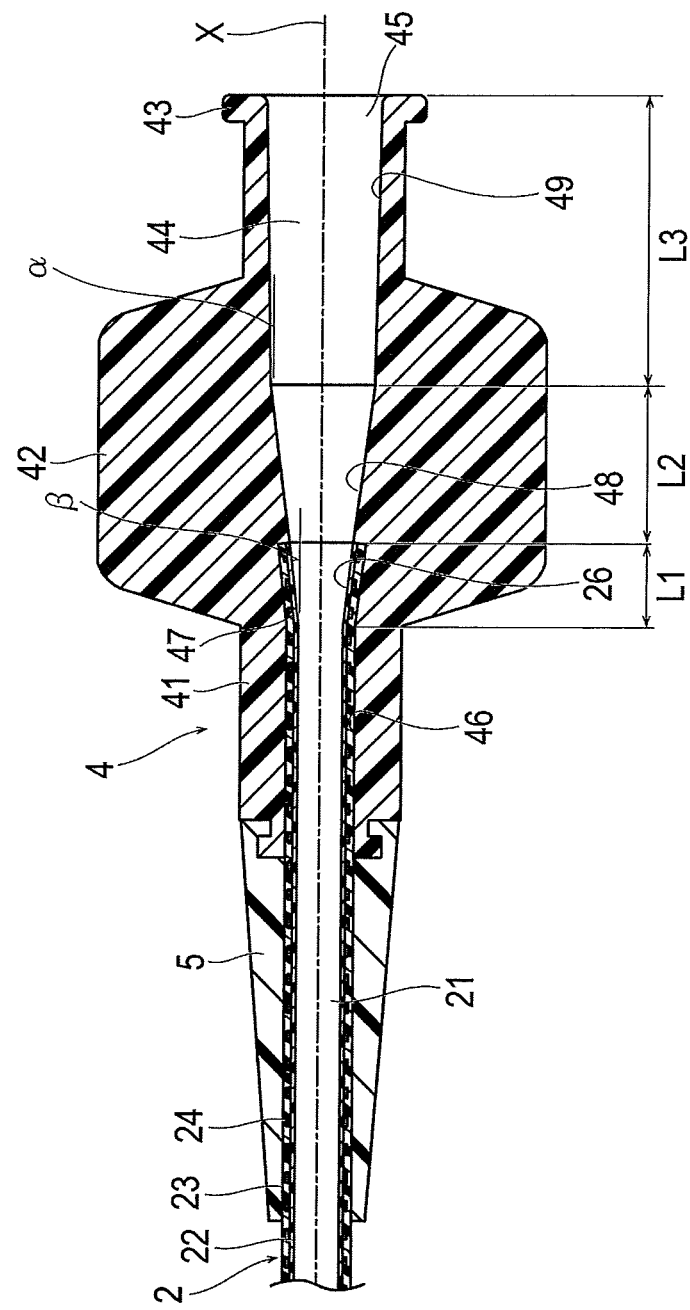
FIG. 4 is a sectional view illustrating a proximal portion of the catheter of the embodiment.

As illustrated in FIGS. 1 and 4, the hub 4 is mounted to the proximal end of the catheter shaft 2. FIGS. 1 and 4 show that the hub 4 is fixed to the catheter shaft 2 so that the distal end portion of the hub 4 axially overlaps the proximal end portion of the catheter shaft 2. A hub lumen 44 communicating with the lumen 21 is formed in the hub 4. A shaft inner surface inclined portion 26 (inclined surface portion) is provided on an inner peripheral surface of a proximal portion of the catheter shaft 2 as shown in FIG. 4. In the illustrated embodiment, the shaft inner surface inclined portion 26 is provided at the proximal-most end portion of the inner peripheral surface of the catheter shaft 2. The shaft inner surface inclined portion 26 widens toward a proximal direction such that the shaft inner surface inclined portion 26 forms an angle (an angle other 180°) with respect to the central axis X of the catheter shaft 2. The shaft inner surface inclined portion 26 is thus not parallel to the central axis X.

An axial length L1 of a portion of the catheter shaft 2, in which the shaft inner surface inclined portion 26 is formed, (i.e., the axial extent of the inclined plane portion 26 measured along the central axis X) is not limited to a specific value. For example, the axial length L1 is 0.5 mm or greater and 3.0 mm or less. If the axial length L1 of the portion, in which the shaft inner surface inclined portion 26 is formed, is excessively short, a medical instrument to be inserted may become caught in the interlock portion in which the catheter shaft 2 and the hub 4 are interlocked together. If the axial length L1 is excessively long, when the catheter shaft 2 is to be formed, the form of the catheter shaft 2 may be distorted.

A long object such as a guide wire, catheters (for example, a PTCA balloon catheter and a stent transport catheter), an endoscope, an ultrasonic probe, or a temperature sensor can be inserted into and removed from the hub 4, and various fluids such as a contrast agent (X-ray contrast agent), a drug solution, and a physiological saline solution can be injected into the hub 4. The hub 4 can be connected to other instruments such as a Y-branch connector, a syringe, and a three-way stopcock.

The hub 4 includes a hollow trunk portion 41; multiple (two in the embodiment) blade portions 42 which protrude outwardly from an outer surface of the trunk portion 41; and a spiral convex portion or spiral outwardly protruding portion 43 that is formed on an outer surface of a proximal portion of the trunk body 41. The trunk portion 41 includes the hub lumen 44 that communicates with the lumen 21 of the catheter shaft 2, and a proximal opening portion 45 that opens at a proximal end of the hub lumen 44. The spiral convex portion 43 can be screwed into a spiral groove formed in a Y-branch connector or the like. The proximal opening portion 45 can be inserted into a distal portion of the Y-branch connector or the like.

A shaft holding portion 46 is provided in a portion of the hub 4 which is positioned on the distal end side of the hub lumen 44. The proximal portion of the catheter shaft 2 is held by and fixed to the shaft holding portion 46.

The hub lumen 44 includes a second hub inner surface inclined portion 49 (inclined surface portion), the inner diameter of which decreases from the proximal opening portion 45 toward a distal direction, and a first hub inner surface inclined portion 48 (inclined surface portion), the inner diameter of which decreases from a distal side or distal end of the second hub inner surface inclined portion 49 toward the distal direction. In the illustrated embodiment shown in FIG. 4, the first hub inner surface inclined portion 48 follows immediately from the distal end of the second hub inner surface inclined portion 49.

The second hub inner surface inclined portion 49 is configured of a female luer taper to which a male luer taper, which is formed on an outer peripheral surface of a cylindrical portion of a Y-branch connector, a syringe, or a three-way stopcock, can be fitted. According to the ISO standards, the taper ratio of the second hub inner surface inclined portion 49 is defined to 6%, that is, an inclination angle α of the second hub inner surface inclined portion 49 with respect to the central axis X is defined to approximately 3.4 degrees. According to the ISO 594-1 standards, a length L3 of the second hub inner surface inclined portion 49 along the central axis X is 7.5 mm or greater.

The inner diameter of the first hub inner surface inclined portion 48 decreases toward the distal direction at a ratio greater than that of the second hub inner surface inclined portion 49. For this reason, when a medical instrument is inserted from a proximal side of the hub 4, the first hub inner surface inclined portion 48 serves to guide the medical instrument, which has been received via the second hub inner surface inclined portion 49, to the lumen 21 of the catheter shaft 2.

The first hub inner surface inclined portion 48 is formed continuously and smoothly from the shaft inner surface inclined portion 26 in a non-stepwise manner on a proximal side or proximal end of the shaft holding portion 46 while being at the same inclination angle β as that of the shaft inner surface inclined portion 26 of the catheter shaft 2 with respect to the central axis X. The hub 4 does not cover an inner peripheral surface of the shaft inner surface inclined portion 26 of the catheter shaft 2 in an interlock portion between the hub 4 and the catheter shaft 2. That is, the inner peripheral surface of the shaft inclined plane 26 is uncovered or exposed.

The material forming the hub 4 is not limited to a specific material. For example, the hub 4 may be formed of hard resin such as polycarbonate, polyethylene, polypropylene, polyamide, polyester, or a polyamide elastomer.

A length L2 of the first hub inner surface inclined portion 48 along the direction of the central axis X plus a length L1 of the hub shaft inclined plane 26 along the direction of the central axis X is not limited to a specific value. For example, the length L2 plus L1 is 2 mm to 20 mm, preferably 4 mm to 12 mm, and more preferably 5 mm to 8 mm.

The inclination angle β of the first hub inner surface inclined portion 48 with respect to the central axis X is not limited to a specific value. For example, the inclination angle β is greater than 0 degrees and less than or equal to 13 degrees, preferably 2 degrees to 10 degrees, and more preferably 4 degrees to 8 degrees.

The anti-kink protector 5 is formed of an elastic material. The interlock portion between the catheter shaft 2 and the hub 4 is coated with the anti-kink protector 5, and thus, the anti-kink protector 5 serves to prevent the bending (kinking) of the vicinity of the interlock portion.

Figure 5:
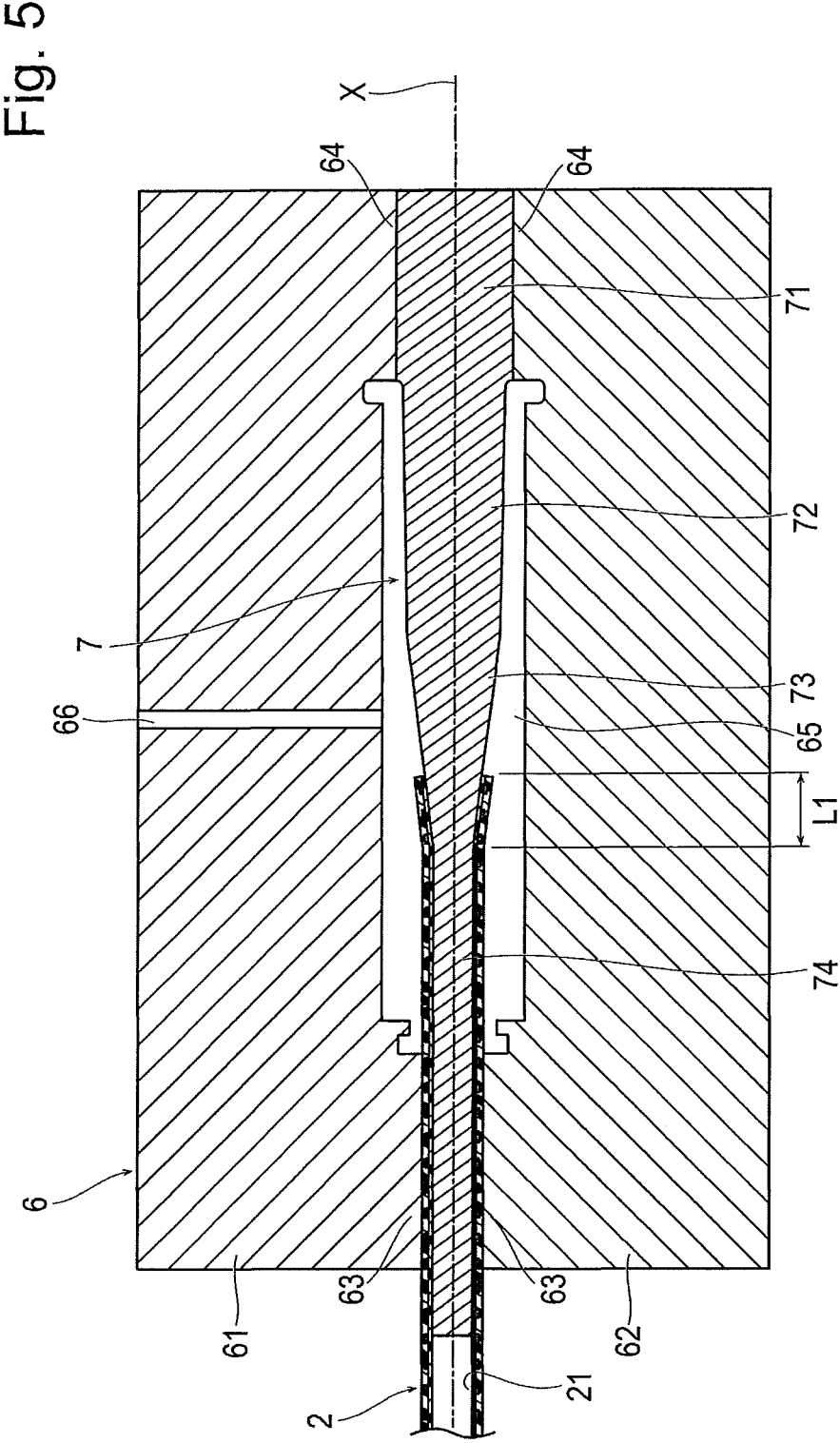
FIG. 5 is a sectional view illustrating a state in which a catheter shaft is installed in a mold.

Hereinafter, a mold 6 used to form the hub 4 of the catheter 1 of the embodiment will be described. The hub 4 is formed by performing injection molding (insert molding) in a state where the catheter shaft 2 is inserted into the mold 6 as illustrated in FIG. 5.

The mold 6 includes a pair of molds, namely an upper mold 61 and a lower mold 62, and a core pin 7 that is inserted into the lumen 21 of the catheter shaft 2 from the proximal portion and holds the catheter shaft 2. Each of the upper mold 61 and the lower mold 62 includes a first holding portion 63 that holds (contacts) a portion of the catheter shaft 2 which has a constant outer diameter, and a second holding portion 64 that holds (contacts) the core pin 7. A cavity 65 to be filled with resin is formed between the first holding portions 63 and the second holding portions 64. A gate 66 is formed in the upper mold 61, and molten resin is injected into the cavity 65 via the gate 66. The upper mold 61 and the lower mold 62 can be heated by heating means such as a heater. Runners may be provided in the mold. Either cold runners or hot runners may be molded.

The core pin 7 includes a core pin proximal portion 71 that is held (contacted) by the second holding portions 64; a proximal tapered portion 72 that extends from the core pin proximal portion 71 toward the distal direction and that possesses an outer diameter that decreases toward the distal direction; a distal tapered portion 73 that extends from the proximal tapered portion 72 toward the distal direction and that possesses an outer diameter that decreases toward the distal direction; and a core pin distal portion 74 that extends from the distal tapered portion 73 toward the distal portion and whose outer diameter does not change (i.e., the outer diameter of the core pin distal portion 74 is constant along its length).

The core pin proximal portion 71 is interposed between and held (contacted) by the second holding portions 64 of the mold 6. The proximal tapered portion 72 is a portion in which the second hub inner surface inclined portion 49 of the hub 4 is formed. The proximal tapered portion 72 possesses a shape to define the second hub inner surface inclined portion 49 upon molding. As a result, the inclination angle of the proximal tapered portion 72 with respect to the central axis X is approximately 3.4 degrees which is the same as that of the second hub inner surface inclined portion 49. The distal tapered portion 73 is a portion in which the first hub inner surface inclined portion 48 of the hub 4 is formed. The distal tapered portion 73 possesses a shape to define the first hub inner surface inclined portion 48 upon molding. As a result, the inclination angle of the distal tapered portion 73 with respect to the central axis X is the same as the inclination angle β of the first hub inner surface inclined portion 48. The core pin distal portion 74 is a portion that is inserted into the catheter shaft 2 held by the first holding portions 63. The outer diameter of the core pin distal portion 74 is substantially the same as the inner diameter of the catheter shaft 2.

Hereinafter, a method of forming the hub 4 via the mold 6 will be described.

First, the catheter shaft 2 is prepared. The shaft inner surface inclined portion 26 (refer to FIG. 4), which is a part of the catheter 1 formed as a finished product, is not yet formed in the catheter shaft 2. The inner diameter of the proximal portion of the catheter shaft 2 is constant in an axial direction. Subsequently, the core pin 7 is inserted into the lumen 21 of the catheter shaft 2 from the proximal portion. As a result, the core pin distal portion 74 is positioned inside the lumen 21 of the catheter shaft 2, and a distal portion of the distal tapered portion 73 penetrates into (is positioned in) the lumen 21 only by the length L1, and widens the inner diameter of the proximal portion of the catheter shaft 2 such that the proximal portion is outwardly tapered. An inner peripheral surface of a widened portion of the catheter shaft 2 finally acts as the shaft inner surface inclined portion 26. Thereafter, as illustrated in FIG. 5, the catheter shaft 2 and the core pin 7 are interposed between the heated upper mold 61 and the heated lower mold 62, the catheter, shaft 2 is held by the first holding portions 63, and the core pin 7 is held by the second holding portions 64.

Figure 6:
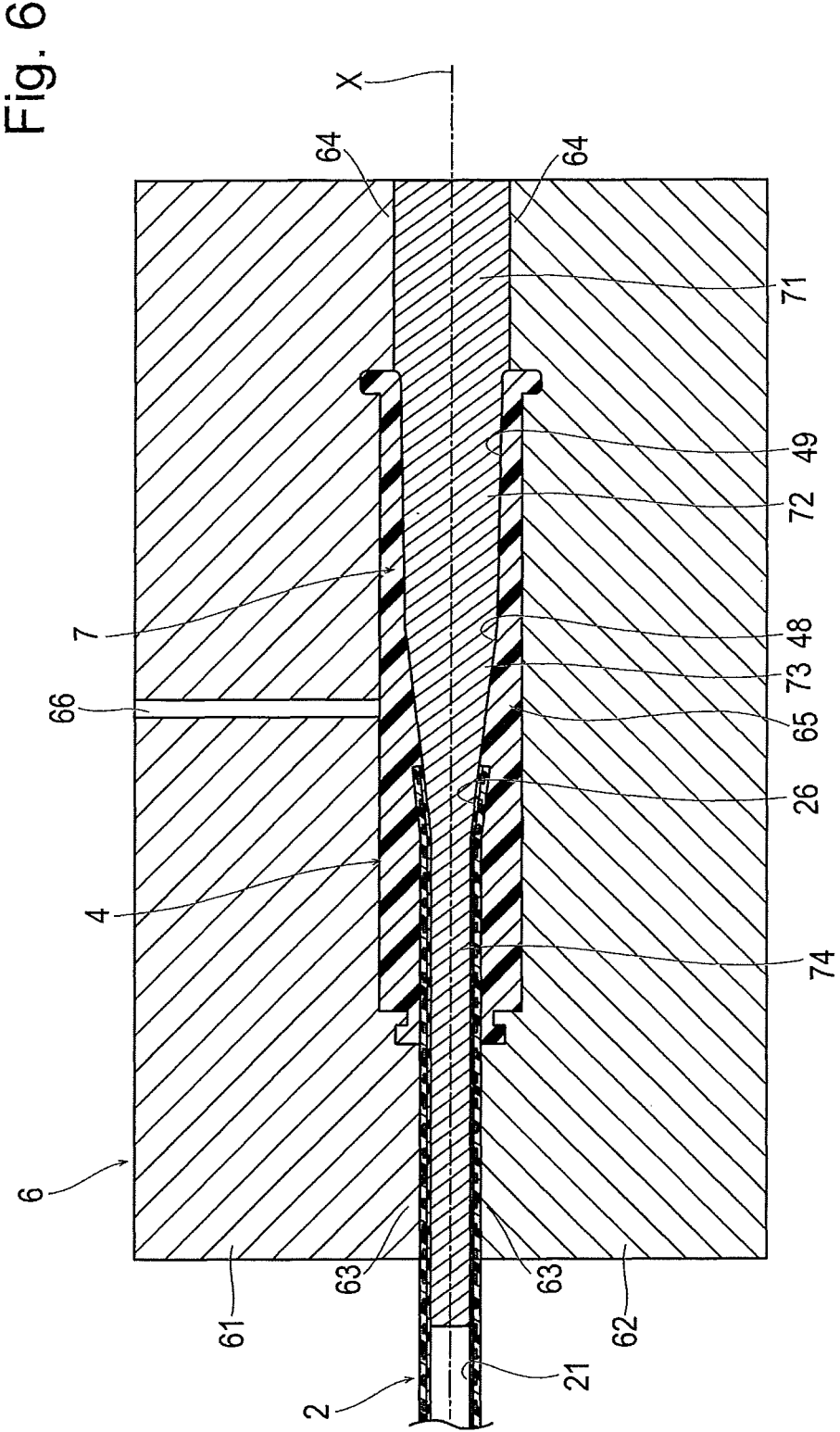
FIG. 6 is a sectional view illustrating a state in which a hub is injection-molded.

Subsequently, molten resin is injected into the cavity 65 of the mold 6 via the gate 66. Thereafter, the molten resin cools and hardens inside the mold 6, and as illustrated in FIG. 6, the hub 4 is formed in a state of being fixedly attached to the catheter shaft 2. After the hub 4 is formed, the upper mold 61 and the lower mold 62 are opened, the core pin 7 is pulled out from the hub 4 and the catheter shaft 2 toward the proximal direction, and the hub 4 fixedly attached to the catheter shaft 2 is finished. The catheter 1 is finished by attaching the soft tip 3 and the strain relief 5 to this molded component. It is also possible that before the hub 4 is formed, the soft tip 3 may be attached to the catheter shaft 2.

At a position at which the distal tapered portion 73 of the core pin 7 is inserted into the catheter shaft 2 and the hub 4 which are formed, the shaft inner surface inclined portion 26 of the catheter shaft 2 is formed continuously and smoothly from the first hub inclined plane 48 of the hub 4 in a non-stepwise manner while the shaft inner surface inclined portion 26 and the first hub inner surface inclined portion 48 are at the same angle with respect to the central axis X. The inner peripheral surface of the shaft inner surface inclined portion 26 is not coated with the material of the hub 4.

Figure 7:
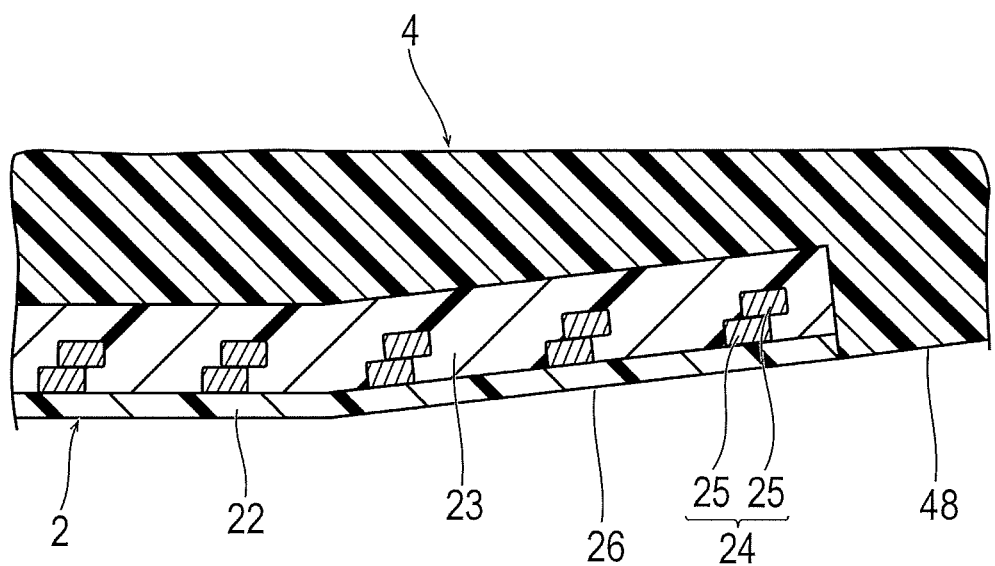
FIG. 7 is a sectional view illustrating a joint portion between the catheter shaft and the hub.
Figure 8:
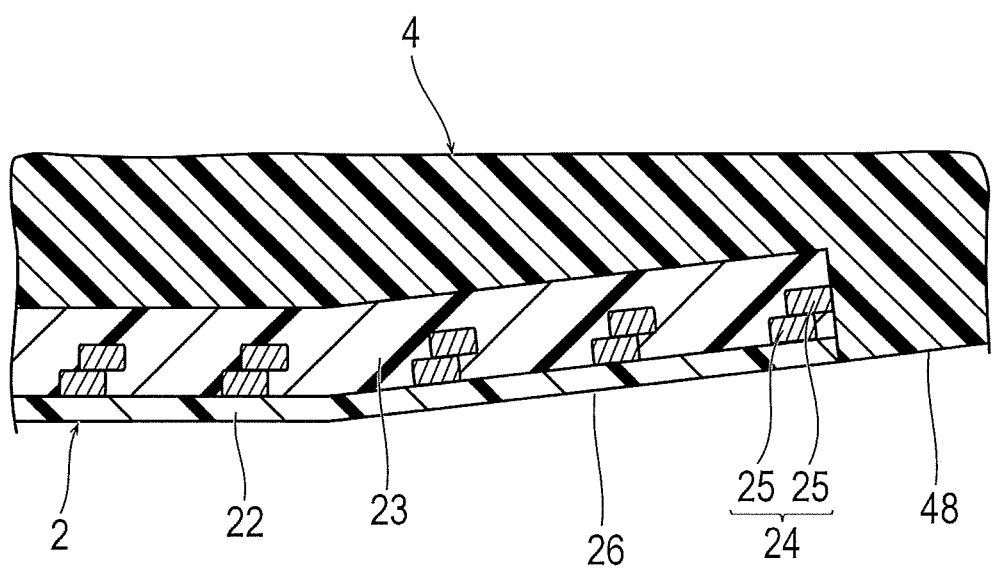
FIG. 8 is a sectional view illustrating a joint portion between the catheter shaft and the hub.
Figure 9:
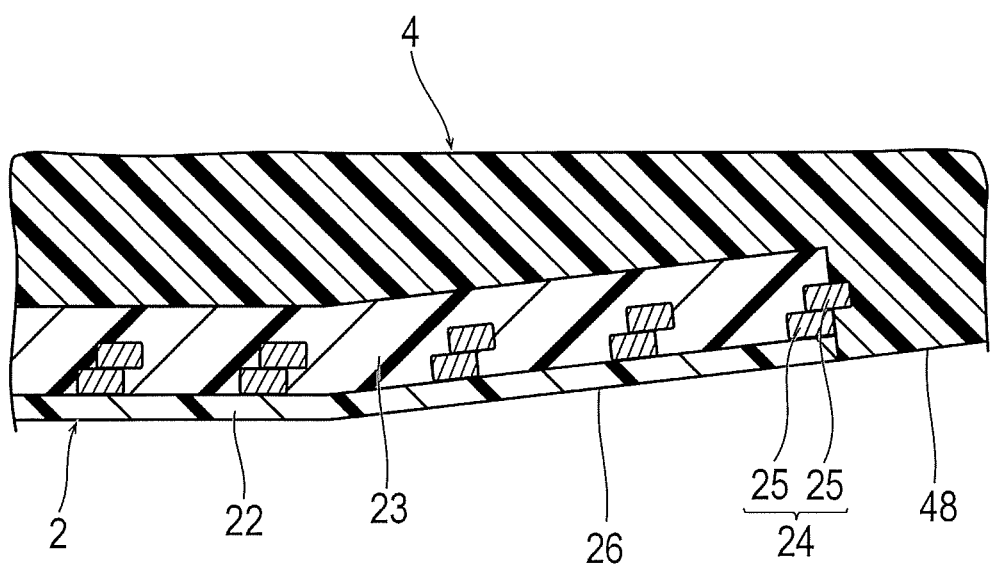
FIG. 9 is a sectional view illustrating a joint portion between the catheter shaft and the hub.

The inner and outer layer resin and the reinforcement filaments 25 in the proximal portion of the catheter shaft 2 of the catheter 1 of the embodiment are simultaneously cut by a blade or the like. That is, the inner and outer resin layers 22, 23 and the reinforcement filaments 25 are cut before the catheter shaft 2 is positioned in the mold 6. For this reason, as illustrated in FIG. 8, a proximal surface of the catheter shaft 2 coincides with the proximal surfaces of the reinforcement filaments 25, the inner layer 22, and the outer layer 23. Since the reinforcement filaments 25 are spirally wrapped, depending on the observed cross-sections, as illustrated in FIG. 7, the reinforcement filaments 25 are disposed inside (i.e., distally of) the inner layer 22 and the outer layer 23, or as illustrated in FIG. 9, the reinforcement filaments 25 protrude further toward the proximal side than the inner layer 22 and the outer layer 23. The reason the reinforcement filaments 25 protrude from (i.e., proximally beyond) the inner layer 22 and the outer layer 23 is that the spirally wrapped reinforcement filaments 25 tend to restore to a straight shape on a cut surface of proximal ends of the inner layer 22 and the outer layer 23.

If the catheter shaft 2 was constructed so that the inner layer 22 sticks out further toward the proximal side than the outer layer 23, when hub resin is injected, the inner layer 22 may protrude toward the inside of the lumen 21 by being pressed by the hub resin. In this case, there is a possibility that a medical instrument in use is caught in the protruding inner layer 22, damage to a medical instrument occurs, or slide resistance increases. In contrast, in the embodiment disclosed here, since proximal portions of the inner layer 22 and the outer layer 23 coincide with each other, when the hub resin is injected, the inner layer 22 is unlikely to protrude toward the inside of the lumen 21, and it is possible to prevent the occurrence of damage to a medical instrument inserted into the lumen 21, or it is possible to reduce the slide resistance of the medical instrument.

If the catheter shaft 2 was constructed so that the proximal portion of the catheter shaft 2 includes a portion in which only the inner layer 22 and the outer layer 23 are provided and the reinforcement portion 24 is not provided, it is more difficult for the portion to maintain a true circle during the insertion of the core pin 7 than other portions including the reinforcement portion 24, and in the catheter 1 having a thin wall, a portion not including the reinforcement portion 24 may be deformed by a hard medical instrument or a medical instrument with large dimensions, which is a problem. In contrast, in the embodiment disclosed here, since the reinforcement portion 24 is provided up to the proximal portions of the inner layer 22 and the outer layer 23, the catheter shaft 2 maintains a true circle during the insertion of the core pin 7, and the shapes of the catheter shaft 2 and the shape of the hub 4 are stable. In addition, in the embodiment disclosed here, since the reinforcement portion 24 is provided up to the proximal portions of the inner layer 22 and the outer layer 23, even if a hard medical instrument or a medical instrument with large dimensions is inserted into the catheter shaft 2, deformation of the catheter shaft 2 is prevented by the reinforcement portion 24.

In a case where the reinforcement portion 24 is provided up to the proximal portions of the inner layer 22 and the outer layer 23, since the reinforcement portion 24 is in direct contact with the molten resin on the proximal surface of the catheter shaft 2 during injection molding, the reinforcement portion 24 bites into the molten resin. Thus, a portion of the reinforcement portion 24 is embedded in the resin forming the hub. As a result, the pressure resistance of the catheter 1 and the durability of the catheter 1 against deformation are improved.

If the inclination angle of the shaft inner surface inclined portion 26 of the catheter shaft 2 is set to 0°, the catheter shaft 2 is strongly affected by the pressurized molten resin inside the mold 6, and even if there is the core pin 7 inside the catheter shaft 2, the diameter of the catheter shaft 2 is likely to be decreased such that the proximal portion of the catheter shaft 2 collapses inward. If the diameter of the catheter shaft 2 is decreased such that the proximal portion of the catheter shaft 2 collapses inward, the inner peripheral surface of the proximal portion of the catheter shaft 2 and an inner peripheral surface of the hub 4 interlocked thereto do not have the same angle with respect to the central axis X, a step is formed therebetween, and the inner peripheral surface of the proximal portion of the catheter shaft 2 is not formed continuously from the inner peripheral surface of the hub 4. There is a possibility that air inside the mold 6 is not suitably released, air entrapment occurs in the hub 4, and the shape of the hub 4 becomes non-uniform. In this case, if a medical instrument such as a balloon catheter is inserted into the catheter 1, slide resistance increases, and separation or damage is likely to occur in the interlock portion between the catheter shaft 2 and the hub 4.

If the inclination angle of the shaft inner surface inclined portion 26 of the catheter shaft 2 is excessively large, the proximal portion of the catheter shaft 2 is excessively open, the molten resin is likely to penetrate between the core pin 7 and the catheter shaft 2 along the core pin 7. If the molten resin penetrates between the core pin 7 and the catheter shaft 2, the material of the hub 4 is positioned on the inner peripheral surface of the shaft inner surface inclined portion 26 of the catheter shaft 2. In this case, when a medical instrument such as a balloon catheter is inserted into the catheter 1, insertion resistance is not so great. In contrast, when the medical instrument is pulled out, slide resistance increases, and separation such as the hub 4 being turned up from the catheter shaft 2, or damage is likely to occur. If the inclination angle of the shaft inner surface inclined portion 26 of the proximal portion of the catheter shaft 2 is excessively large, air entrapment is likely to occur in the hub 4 in the vicinity of a portion of the catheter shaft 2, the angle of which changes (portion of the catheter shaft 2, the outer diameter of which starts to change), and the shape of the hub 4 becomes non-uniform, which is likely to be a cause of an increase in slide resistance, separation, or damage.

Accordingly, if the inclination angle β of the shaft inner surface inclined portion 26 and the first hub inner surface inclined portion 48 with respect to the central axis X is set to a suitable value, the molten resin suitably reaches the core pin 7 and the catheter shaft 2, and air inside the mold 6 is suitably released. As a result, the shaft inner surface inclined portion 26 can be formed continuously and smoothly from the first hub inner surface inclined portion 48 in a non-stepwise manner while the shaft inner surface inclined portion 26 and the first hub inner surface inclined portion 48 are at the same angle with respect to the central axis X. In order to suitably form the shaft inner surface inclined portion 26 and the first hub inner surface inclined portion 48, the inclination angle β is set to be greater than 0 degrees and 13 degrees or less, preferably 2 degrees to 10 degrees, and more preferably 4 degrees to 8 degrees.

As described above, the catheter 1 of the embodiment disclosed here includes the catheter shaft 2 in which the lumen 21 is formed, and the hub 4 in which the hub lumen 44 communicating with the lumen 21 is formed, and which is provided on the proximal side of the catheter shaft 2. The catheter shaft 2 includes the shaft inner surface inclined portion 26 which is formed on the inner peripheral surface of the proximal portion, and the diameter of which increases toward the proximal direction such that the shaft inner surface inclined portion 26 has an angle with respect to the central axis X of the catheter 1. The hub 4 includes the first hub inner surface inclined portion 48 that is continuous from the shaft inner surface inclined portion 26 while being at the same inclination angle β as the angle of the shaft inner surface inclined portion 26 with respect to the central axis X, and the second hub inner surface inclined portion 49 which is provided on a proximal side of the first hub inner surface inclined portion 48, and the inner diameter of which increases toward the proximal direction such that the second hub inner surface inclined portion 49 has the inclination angle α different from the angle of the first hub inner surface inclined portion 48 with respect to the central axis X. The hub 4 does not cover the inner peripheral surface of the catheter shaft 2 in the interlock portion in which the catheter shaft 2 and the hub 4 are interlocked together. In the catheter 1 having such a configuration, since the catheter shaft 2 and the hub 4 are interlocked together at the position of an inclined portion with which a medical instrument is unlikely to come into contact, and the inner peripheral surfaces of the catheter shaft 2 and the hub 4 in the interlock portion have the same inclination angle β, the slide resistance of the medical instrument against a lumen of the catheter 1 is reduced. Since the hub 4 does not cover the inner peripheral surface of the catheter shaft 2 in the interlock portion between the hub 4 and the catheter shaft 2, when a medical instrument or the like is slid inside the lumen 21, particularly, when the medical instrument or the like is pulled backward, the separation of the hub resin is unlikely to occur, and it is possible to reduce deformation of or damage to the catheter 1 or the medical instrument which is caused by slide resistance or separation. Accordingly, even if a medical instrument such as a balloon catheter is repeatedly inserted into and removed from the catheter 1, deformation of or damage to the catheter 1 or the medical instrument is unlikely to occur.

The catheter shaft 2 includes the inner layer 22; the outer layer 23 that is disposed an outer peripheral surface side of the inner layer 22; and the reinforcement filaments 25 which are disposed on the outer surface of the inner layer 22 and are embedded in the outer layer 23. Since the reinforcement filaments 25 are provided in the catheter shaft 2, deformation of the catheter shaft 2 is prevented, and separation between the hub 4 and the catheter shaft 2 is unlikely to occur. As a result, it is possible to prevent deformation of or damage to the catheter 1 or a medical instrument. In a case where the hub 4 is molded via injection molding, the resin which is the material of the hub 4 is likely to penetrate into the catheter shaft 2. In contrast, since the reinforcement filaments 25 are provided in the catheter shaft 2, the proximal portion of the catheter shaft 2 is unlikely to be deformed, and it is possible to prevent the penetration of the resin into the catheter shaft 2. For this reason, separation between the hub 4 and the catheter shaft 2 is unlikely to occur, and it is possible to reduce deformation of or damage to the catheter 1 or a medical instrument.

The reinforcement filaments 25 may be in contact with the hub 4 on the proximal surface of the catheter shaft 2. As a result, the hub 4 and the catheter shaft 2 are rigidly interlocked together, and the pressure resistance of the catheter 1 and the durability of the catheter 1 against deformation are improved.

At least a portion of the reinforcement filaments 25 may protrude further toward the proximal side than the inner layer 22 and the outer layer 23, and may bite into the hub 4. As a result, the hub 4 and the catheter shaft 2 are more rigidly interlocked together, and the pressure resistance of the catheter 1 and the durability of the catheter 1 against deformation are further improved.

The axial length L1 of the portion of the catheter shaft 2, in which the shaft inner surface inclined portion 26 is formed, may be set to 0.5 mm or greater and 3.0 mm or less. If the axial length L1 of the portion, in which the shaft inner surface inclined portion 26 is formed, is excessively short, a medical instrument to be inserted may become caught in the interlock portion in which the catheter shaft 2 and the hub 4 are interlocked together. If the axial length L1 is excessively long, when the catheter shaft 2 is to be formed, the form of the catheter shaft 2 may be distorted.

The inclination angle f3 of the shaft inner surface inclined portion 26 with respect to the central axis X of the catheter 1 may be set to exceed 0° and to be 13° or less. If the inclination angle of the shaft inner surface inclined portion 26 with respect to the central axis X is 0°, when the hub 4 is to be molded via injection molding, the inner pressure of the mold 6 is likely to cause the distortion of the proximal portion of the catheter shaft 2 such that the proximal portion of the catheter shaft 2 collapses inward. If the inclination angle β of the shaft inner surface inclined portion 26 with respect to the central axis X is excessively large, during injection molding, the resin of the hub 4 is likely to penetrate into the catheter shaft 2.

The catheter shaft 2 may be formed of a material containing polytetrafluoroethylene. As a result, the catheter shaft 2 is unlikely to have affinity with the material of the hub 4, and is likely to separate therefrom; however, according to the present invention, it is possible to prevent the occurrence of separation.

Example

Hereinafter, an example of the catheter disclosed here will be described.

A catheter, in which the inclination angle of a first hub inner surface inclined portion and a shaft inner surface inclined portion with respect to a central axis was 6.7 degrees, was produced. An inner layer of a catheter shaft was formed of polytetrafluoroethylene (PTFE). A reinforcement portion was formed by braiding flat filaments made of stainless steel. An outer layer was formed of a nylon elastomer. The catheter shaft was installed in a mold, and a hub was formed of a nylon elastomer via injection molding. As a result, an example was obtained. As such, the shaft inner surface inclined portion was formed continuously and smoothly from the first hub inner surface inclined portion in a non-stepwise manner while the shaft inner surface inclined portion and the first hub inner surface inclined portion were at the same angle with respect to the central axis.

Comparative Example 1 is Mach 1 (registered trademark) which is a guiding catheter manufactured by Boston Scientific Corporation. Comparative Example 2 is Brite Tip (registered trademark) which is a guiding catheter manufactured by CORDIS Corporation. In the catheter of Comparative Example 1, an inner peripheral surface in an interlock portion between a catheter shaft and a hub was not covered with hub resin, the angle of a shaft inner surface inclined portion was different from that of a first hub inner surface inclined portion adjacent thereto, and a step was formed therebetween. In the catheter of Comparative Example 2, an inner peripheral surface of a shaft inner surface inclined portion in an interlock portion between a catheter shaft and a hub was covered with resin, and a step was formed at the boundary between a shaft surface and a hub surface on the inner peripheral surface.

Hereinafter, a guide wire (Radifocus (registered trademark) guide wire M) manufactured by Terumo Co. LTD. was inserted into the catheters of the example, Comparative Example 1, and Comparative Example 2, and the slidability of the guide wire was confirmed by the sensing of a hand. Table 1 illustrates results.

TABLE 1

|  | Example | Comparative Example 1 | Comparative Example 2 |
|---|---|---|---|
| slidability | ○ | Δ | X |

As a result, when the guide wire was either inserted into or pulled backward from the catheter of the example according to the disclosure here, almost no slide resistance of the guide wire against an interlock portion between the hub and the catheter shaft was sensed.

In contrast, when the guide wire was inserted into the catheter of Comparative Example 1, almost no slide resistance of the guide wire against the interlock portion between the hub and the catheter shaft was sensed, but in contrast, when the guide wire was pulled backward, slight slide resistance of the guide wire against the interlock portion was sensed.

When the guide wire was either inserted into or pulled backward from the catheter of Comparative Example 2, the slide resistance of the guide wire against the step of the interlock portion was sensed.

The present invention is not limited to only the above-described embodiment having the features described, and persons skilled in the art can make changes to the embodiment in various forms within the technical concept of the present invention. The catheter is not limited to a specific use insofar as the catheter is inserted into and used in a biological lumen. The biological lumen is not limited to a blood vessel, and may be a vessel, a ureter, a biliary duct, a oviduct, a hepatic duct, or the like.

The catheter shaft 2 of the embodiment includes the inner layer 22; the reinforcement portion 24; and the outer layer 23; however, the structure of the catheter shaft is not limited to that in the embodiment, and the catheter shaft may be formed of a single material.

The detailed description above describes a catheter according to an embodiment disclosed by way of example. The invention here is not limited, however, to the precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A catheter comprising:
    a catheter shaft in which a lumen is formed, the catheter shaft including a proximal portion;
    a hub in which a hub lumen communicating with the lumen of the catheter shaft is formed, the lumen of the catheter shaft defining an inner peripheral surface of the catheter shaft, the hub being provided on a proximal portion of the catheter shaft;
    the catheter shaft including a shaft inner surface inclined portion which is formed on an inner peripheral surface of the proximal portion of the catheter shaft, the shaft inner surface inclined portion possessing a first inner diameter increasing toward a proximal direction such that the shaft inner surface inclined portion forms an inclination angle with respect to a central axis of the catheter that is greater than an inclination angle of a portion of the inner peripheral surface of the catheter shaft other than the shaft inner surface inclined portion and is equal to or less than 13 degrees;
    the hub including a first hub inner surface inclined portion that is continuous from the shaft inner surface inclined portion and that is inclined at an inclination angle with respect to the central axis of the catheter that is the same as the inclination angle of the shaft inner surface inclined portion;
    the shaft inner surface inclined portion on the inner peripheral surface of the proximal portion of the catheter shaft extending continuously and smoothly from the first hub inner surface inclined portion of the hub in a non-stepwise manner;
    the hub also including a second hub inner surface inclined portion on a proximal side of the first hub inner surface inclined portion, the second hub inner surface inclined portion possessing a second inner diameter which increases toward the proximal direction such that the second hub inner surface inclined portion forms an inclination angle with respect to the central axis of the catheter that is smaller than the inclination angle of the first hub inner surface inclined portion;
    the hub not covering the inner peripheral surface of the proximal portion of the catheter shaft in an interlock portion in which the catheter shaft and the hub are interlocked together; and
    the catheter shaft, including the proximal portion, being comprised of an inner layer; an outer layer that is disposed on an outer peripheral surface side of the inner layer; and reinforcement filaments which are disposed between an outer peripheral surface of the inner layer and an inner peripheral surface of the outer layer, wherein at least a portion of the reinforcement filaments protrudes proximally beyond the inner layer and the outer layer, and is embedded in the hub.

2. The catheter according to claim 1, wherein the catheter shaft is formed of a material containing polytetrafluoroethylene.

3. The catheter according to claim 1, wherein an axial length of a portion of the catheter shaft, in which the shaft inner surface inclined portion is formed, is greater than or equal to 0.5 mm and less than or equal to 3.0 mm.

4. The catheter according to claim 1, wherein an inner peripheral surface of the inner layer is the inner peripheral surface of the catheter shaft.

5. The catheter according to claim 1, further comprising an anti-kink protector fixed to a distal end portion of the hub and axially overlying a portion of the catheter shaft.

6. A catheter comprising:
    a catheter shaft possessing a proximal end portion, and an axially extending catheter shaft lumen passing through the catheter shaft, the catheter shaft lumen being surrounded by an inner peripheral surface of the catheter shaft;
    a hub fixed to the proximal end portion of the catheter shaft so that a distal end portion of the hub axially overlaps the proximal end portion of the catheter shaft in an overlap region, and a hub lumen inside the hub, the hub lumen possessing an inner peripheral surface surrounding the hub lumen, the hub communicating with the catheter shaft lumen;
    a proximal-most end portion of the inner peripheral surface of the catheter shaft including a first inclined portion possessing a first catheter shaft inner diameter gradually increasing at an inclination angle in a proximal direction that is greater than an inclination angle of a portion of the inner peripheral surface of the catheter shaft other than the first inclined portion and is equal to or less than 13 degrees;
    the inner peripheral surface of the hub including a first inclined portion possessing a first hub inner diameter gradually increasing at an inclination angle in the proximal direction, the inclination angle of the first inclined portion of the inner peripheral surface of the hub being the same as the inclination angle of the first inclined portion of the inner peripheral surface of the catheter shaft;
    a proximal-most end of the first inclined portion of the inner peripheral surface of the catheter shaft and a distal-most end of the first inclined portion of the inner peripheral surface of the hub immediately adjoining one another;
    the proximal-most end of the first inclined portion of the inner peripheral surface of the catheter shaft extending continuously and smoothly from the distal-most end of the first inclined portion of the inner peripheral surface of the hub in a non-stepwise manner;
    the inner peripheral surface of the hub including a second inclined portion possessing a second hub inner diameter gradually increasing at an inclination angle in the proximal direction, the inclination angle of the first inclined portion of the inner peripheral surface of the hub being greater than the inclination angle of the second inclined portion of the inner peripheral surface of the hub;

the second inclined portion of the inner peripheral surface of the hub being positioned proximally of the first inclined portion of the inner peripheral surface of the hub;

the hub being made of a material that does not cover the inner peripheral surface of the catheter shaft in the overlap region; and the catheter shaft, including the proximal end portion, being comprised of an inner layer; an outer layer disposed on an outer peripheral surface side of the inner layer; and a reinforcement filament disposed between an outer peripheral surface of the inner layer and an inner peripheral surface of the outer layer, wherein at least a portion of the reinforcement filament protrudes proximally beyond the inner layer and the outer layer, and is embedded in the hub.

7. The catheter according to claim 6, wherein the catheter shaft is formed of a material containing polytetrafluoroethylene.

8. The catheter according to claim 6, wherein an axial length of the first inclined portion of the inner peripheral surface of the catheter shaft is greater than or equal to 0.5 mm and less than or equal to 3.0 mm.

9. The catheter according to claim 6, further comprising an anti-kink protector fixed to a distal end portion of the hub and axially overlying a portion of the catheter shaft.

10. The catheter according to claim 6, wherein an inner peripheral surface of the inner layer is the inner peripheral surface of the catheter shaft.

\* \* \* \* \*